United States Patent
Leung et al.

(10) Patent No.: US 9,695,241 B2
(45) Date of Patent: *Jul. 4, 2017

(54) ANG2 ANTIBODIES

(71) Applicant: Eli Lilly and Company, Indianapolis, IN (US)

(72) Inventors: Donmienne Doen Mun Leung, San Diego, CA (US); Jianghuai Xu, San Diego, CA (US)

(73) Assignee: Eli Lilly and Company, Indianapolis, IN (US)

(*) Notice: Subject to any disclaimer, the term of this patent is extended or adjusted under 35 U.S.C. 154(b) by 216 days.

This patent is subject to a terminal disclaimer.

(21) Appl. No.: 14/709,514

(22) Filed: May 12, 2015

(65) Prior Publication Data
US 2015/0329627 A1    Nov. 19, 2015

Related U.S. Application Data

(60) Provisional application No. 62/000,253, filed on May 19, 2014.

(51) Int. Cl.
*A61K 39/395* (2006.01)
*A61K 39/00* (2006.01)
*C12P 21/06* (2006.01)
*C12P 21/08* (2006.01)
*C07H 21/02* (2006.01)
*C07K 16/28* (2006.01)
*C07K 16/22* (2006.01)

(52) U.S. Cl.
CPC ...... *C07K 16/2863* (2013.01); *A61K 39/3955* (2013.01); *C07K 16/22* (2013.01); *A61K 2039/505* (2013.01); *A61K 2039/507* (2013.01); *C07K 2317/14* (2013.01); *C07K 2317/34* (2013.01); *C07K 2317/41* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 9,580,499 | B2 * | 2/2017 | Leung | C07K 16/22 |
|---|---|---|---|---|
| 2006/0246071 | A1 | 11/2006 | Green et al. | |
| 2010/0159587 | A1 | 6/2010 | Brinkmann et al. | |
| 2011/0027286 | A1 | 2/2011 | Thurston et al. | |

FOREIGN PATENT DOCUMENTS

| WO | WO 2006/068953 A2 | 6/2006 |
|---|---|---|
| WO | WO 2009/097325 A1 | 8/2009 |
| WO | WO 2011/014469 A1 | 2/2011 |

OTHER PUBLICATIONS

Augustin, H. et al., "Control of vascular morphogenesis and homeostasis through the angiopoietin-Tie system," Nature Reviews; 10, pp. 165-177 (2009).
Brown, J., et al., "A Human Monoclonal Anti-ANG2 Antibody Leads to Broad Antitumor Activity in Combination with VEGF Inhibitors and Chemotherapy Agents in Preclinical Models," Mol Cancer Ther; 9(1), pp. 145-156 (2010).
Gerald, D., et al., "Angiopoietin-2: An Attractive Target for Improved Antiangiogenic Tumor Therapy," Cancer Research; 57(1), pp. 1649-1657 (2013).
Daly, C., et al., "Angiopoietin-2 Functions as a Tie2 Agonist in Tumor Models, Where It Limits the Effects of VEGF Inhibition," Cancer Research; 73(1), pp. 108-118 (2013).
Cascone, T., et al., "Targeting the Angiopoietin/Tie2 Pathway: Cutting Tumor Vessels With a Double-Edged Sword?," J. of Clin. Onc.; 30(4), pp. 441-444 (2012).
Demarest, S., et al., "Emerging antibody combinations in oncology," mAbs; 3(4), pp. 338-351 (Jul./Aug. 2011).
Eroglu, Z., et al., "Targeting angiopoietin-2 signaling in cancer therapy," Expert Opinion; 22, pp. 813-825 (2013).
Huang, H., et al., "Targeting the ANGPT-TIE2 pathway in malignancy," Natural Reviews Cancer; 10, pp. 575-585 (2010).
Leow, C., et al., "MEDI3617, a human anti-Angiopoietin 2 monoclonal antibody, inhibits angiogenesis and tumor growth in human tumor xenograft models," Intl. Oncol.; 40(5), pp. 1321-1330 (May 10, 2012).
Rennel, E., et al., "A human neutralising antibody specific to Ang-2 inhibits ocular angiogenesis," Microcirculation; 18 (7), pp. 598-607 (Oct. 2011).
Eklund, L. and Saharinen, P., "Angiopoietin signalinginthevasculature," Experimental Cell Research; 319, pp. 1271-1280 (2013).
Oliner, J., et al., "Suppression of angiogenesis and tumor growth by selective inhibition of angiopoietin-2," Cancer Cell; 6, pp. 507-516 (2004).
Thomas, M., et al., "A Novel Angiopoietin-2 Selective Fully Human Antibody with Potent Anti-Tumoral and Anti-Angiogenic Efficacy and Superior Side Effect Profile Compared to Pan-Angiopoietin-1/-2 Inhibitors," PLOS One; 8(2): e54923 (2013).

* cited by examiner

*Primary Examiner* — Maher Haddad
(74) *Attorney, Agent, or Firm* — Robert B. Johnson

(57) ABSTRACT

The present invention relates to antibodies that bind human angiopoietin-2 (Ang2), and may be useful for treating cancer alone and in combination with VEGF pathway inhibitors, especially cancer driven by VEGFR2 and Ang2, including gastric, hepatocellular carcinoma, ovarian, colorectal, and breast cancers.

13 Claims, No Drawings

SEQUENCE LISTING

<160> NUMBER OF SEQ ID NOS: 13

<210> SEQ ID NO 1
<211> LENGTH: 121
<212> TYPE: PRT
<213> ORGANISM: Artificial Sequence
<220> FEATURE:
<223> OTHER INFORMATION: Synthetic Construct
<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Val Trp Val Arg Gln Ala Pro Gly Gln Gly Leu Glu Trp Met
        35                  40                  45

Gly Tyr Ile Asp Pro Tyr Asn Gly Gly Thr Gly Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Arg Asp Arg Tyr Asp Val Trp Tyr Phe Asp Val Trp Gly
            100                 105                 110

Gln Gly Thr Leu Val Thr Val Ser Ser
            115                 120

<210> SEQ ID NO 2
<211> LENGTH: 447
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Val Trp Val Arg Gln Ala Pro Gly Gln Gly Leu Glu Trp Met
        35                  40                  45

Gly Tyr Ile Asp Pro Tyr Asn Gly Gly Thr Gly Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Arg Asp Arg Tyr Asp Val Trp Tyr Phe Asp Val Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Lys Thr Tyr Thr Cys Asn Val Asp His
    195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Ala Ala Gly Gly Pro Ser
225                 230                 235                 240
```

-continued

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly
            435                 440                 445

<210> SEQ ID NO 3
<211> LENGTH: 107
<212> TYPE: PRT
<213> ORGANISM: Artificial Sequence
<220> FEATURE:
<223> OTHER INFORMATION: Synthetic Construct

<400> SEQUENCE: 3

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Tyr Ile Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg Asp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ser Ser Tyr Pro Pro
                85                  90                  95

Thr Phe Gly Gly Gly Thr Lys Val Glu Ile Lys
            100                 105

<210> SEQ ID NO 4
<211> LENGTH: 214
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Val Ser Ala Ser Val Gly
1               5                   10                  15

Asp Arg Val Thr Ile Thr Cys Lys Ala Ser Gln Asp Val Tyr Ile Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg Asp Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Ser Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 642
<212> TYPE: DNA
<213> ORGANISM: Artificial Sequence
<220> FEATURE:
<223> OTHER INFORMATION: Synthetic Construct

<400> SEQUENCE: 5

```
gacatccaga tgacccagtc tccatcttcc gtgtctgcat ctgtaggaga cagagtcacc      60
atcacttgta aggccagtca ggatgtgtat attgctgtag cctggtatca gcagaaacca     120
gggaaagccc ctaagctcct gatctattgg gcatccaccc gggacactgg ggtcccatca     180
aggttcagcg gcagtggatc tgggacagat ttcactctca ccatcagcag cctgcagcct     240
gaagattttg caacttacta ttgtcaccaa tatagcagct atcctcctac gttcggcgga     300
gggaccaagg tggagatcaa acggactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gc                        642
```

<210> SEQ ID NO 6
<211> LENGTH: 1341

<212> TYPE: DNA
<213> ORGANISM: Artificial Sequence
<220> FEATURE:
<223> OTHER INFORMATION: Synthetic Construct

<400> SEQUENCE: 6

```
caggttcagc tggtgcagtc tggagctgag gtgaagaagc tggggcctc  agtgaaggtc      60
tcctgcaagg cttctggtta ctcattcact gactacaaca tggtgtgggt gcgacaggcc     120
cctggacaag gcttgagtg gatgggatat attgatcctt acaatggtgg tactggctac     180
aaccagaagt tcgagggcag agtcaccatg accacagaca catccacgag cacagcctac     240
atggagctga ggagcctgag atctgacgac acggccgtgt attactgtgc gagaacgagg     300
gataggtacg acgtctggta cttcgatgtc tggggccagg gaaccctggt caccgtctcc     360
tcagcctcca ccaagggccc atcggtcttc ccgctagcgc cctgctccag gagcacctcc     420
gagagcacag ccgccctggg ctgcctggtc aaggactact cccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacgaag     600
acctacacct gcaacgtaga tcacaagccc agcaacacca aggtggacaa gagagttgag     660
tccaaatatg gtcccccatg cccaccctgc ccagcacctg aggccgccgg ggaccatca      720
gtcttcctgt tccccccaaa acccaaggac actctcatga tctcccggac ccctgaggtc     780
acgtgcgtgg tggtggacgt gagccaggaa gaccccgagg tccagttcaa ctggtacgtg     840
gatggcgtgg aggtgcataa tgccaagaca aagccgcggg aggagcagtt caacagcacg     900
taccgtgtgg tcagcgtcct caccgtcctg caccaggact ggctgaacgg caaggagtac     960
aagtgcaagg tctccaacaa aggcctcccg tcctccatcg agaaaaccat ctccaaagcc    1020
aaagggcagc cccgagagcc acaggtgtac accctgcccc catcccagga ggagatgacc    1080
aagaaccagg tcagcctgac ctgcctggtc aaaggcttct accccagcga catcgccgtg    1140
gagtgggaaa gcaatgggca gccggagaac aactacaaga ccacgcctcc cgtgctggac    1200
tccgacggct ccttcttcct ctacagcagg ctaaccgtgg acaagagcag gtggcaggag    1260
gggaatgtct tctcatgctc cgtgatgcat gaggctctgc acaaccacta cacacagaag    1320
agcctctccc tgtctctggg t                                              1341
```

<210> SEQ ID NO 7
<211> LENGTH: 478
<212> TYPE: PRT
<213> ORGANISM: Homo sapiens

<400> SEQUENCE: 7

```
Tyr Asn Asn Phe Arg Lys Ser Met Asp Ser Ile Gly Lys Lys Gln Tyr
1               5                   10                  15

Gln Val Gln His Gly Ser Cys Ser Tyr Thr Phe Leu Leu Pro Glu Met
            20                  25                  30

Asp Asn Cys Arg Ser Ser Ser Pro Tyr Val Ser Asn Ala Val Gln
        35                  40                  45

Arg Asp Ala Pro Leu Glu Tyr Asp Asp Ser Val Gln Arg Leu Gln Val
    50                  55                  60

Leu Glu Asn Ile Met Glu Asn Asn Thr Gln Trp Leu Met Lys Leu Glu
65                  70                  75                  80

Asn Tyr Ile Gln Asp Asn Met Lys Lys Glu Met Val Glu Ile Gln Gln
                85                  90                  95
```

Asn Ala Val Gln Asn Gln Thr Ala Val Met Ile Glu Ile Gly Thr Asn
            100                 105                 110

Leu Leu Asn Gln Thr Ala Glu Gln Thr Arg Lys Leu Thr Asp Val Glu
        115                 120                 125

Ala Gln Val Leu Asn Gln Thr Thr Arg Leu Glu Leu Gln Leu Leu Glu
    130                 135                 140

His Ser Leu Ser Thr Asn Lys Leu Glu Lys Gln Ile Leu Asp Gln Thr
145                 150                 155                 160

Ser Glu Ile Asn Lys Leu Gln Asp Lys Asn Ser Phe Leu Glu Lys Lys
                165                 170                 175

Val Leu Ala Met Glu Asp Lys His Ile Ile Gln Leu Gln Ser Ile Lys
            180                 185                 190

Glu Glu Lys Asp Gln Leu Gln Val Leu Val Ser Lys Gln Asn Ser Ile
        195                 200                 205

Ile Glu Glu Leu Glu Lys Lys Ile Val Thr Ala Thr Val Asn Asn Ser
    210                 215                 220

Val Leu Gln Lys Gln Gln His Asp Leu Met Glu Thr Val Asn Asn Leu
225                 230                 235                 240

Leu Thr Met Met Ser Thr Ser Asn Ser Ala Lys Asp Pro Thr Val Ala
                245                 250                 255

Lys Glu Glu Gln Ile Ser Phe Arg Asp Cys Ala Glu Val Phe Lys Ser
            260                 265                 270

Gly His Thr Thr Asn Gly Ile Tyr Thr Leu Thr Phe Pro Asn Ser Thr
        275                 280                 285

Glu Glu Ile Lys Ala Tyr Cys Asp Met Glu Ala Gly Gly Gly Gly Trp
    290                 295                 300

Thr Ile Ile Gln Arg Arg Glu Asp Gly Ser Val Asp Phe Gln Arg Thr
305                 310                 315                 320

Trp Lys Glu Tyr Lys Val Gly Phe Gly Asn Pro Ser Gly Glu Tyr Trp
                325                 330                 335

Leu Gly Asn Glu Phe Val Ser Gln Leu Thr Asn Gln Gln Arg Tyr Val
            340                 345                 350

Leu Lys Ile His Leu Lys Asp Trp Glu Gly Asn Glu Ala Tyr Ser Leu
        355                 360                 365

Tyr Glu His Phe Tyr Leu Ser Ser Glu Glu Leu Asn Tyr Arg Ile His
    370                 375                 380

Leu Lys Gly Leu Thr Gly Thr Ala Gly Lys Ile Ser Ser Ile Ser Gln
385                 390                 395                 400

Pro Gly Asn Asp Phe Ser Thr Lys Asp Gly Asp Asn Asp Lys Cys Ile
                405                 410                 415

Cys Lys Cys Ser Gln Met Leu Thr Gly Gly Trp Trp Phe Asp Ala Cys
            420                 425                 430

Gly Pro Ser Asn Leu Asn Gly Met Tyr Tyr Pro Gln Arg Gln Asn Thr
        435                 440                 445

Asn Lys Phe Asn Gly Ile Lys Trp Tyr Tyr Trp Lys Gly Ser Gly Tyr
    450                 455                 460

Ser Leu Lys Ala Thr Thr Met Met Ile Arg Pro Ala Asp Phe
465                 470                 475

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 8

Lys Ala Ser Gln Asp Val Tyr Ile Ala Val Ala
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Tyr Trp Ala Ser Thr Arg Asp Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

His Gln Tyr Ser Ser Tyr Pro Pro Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Gly Tyr Ser Phe Thr Asp Tyr Asn Met Val
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Tyr Ile Asp Pro Tyr Asn Gly Gly Thr Gly Tyr Asn Gln Lys Phe Glu
1               5                   10                  15

Gly

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Ala Arg Thr Arg Asp Arg Tyr Asp Val Trp Tyr Phe Asp Val
1               5                   10
```

ANG2 ANTIBODIES

The present invention relates to the field of medicine. More particularly, the present invention relates to antibodies that bind human angiopoietin-2 (Ang2), and may be useful for treating cancer, especially tumor metastasis, and in combination with human vascular endothelial growth factor receptor 2 (VEGFR2) inhibitors for solid tumors driven by VEGFR2 and Ang2, including gastric, hepatocellular carcinoma, ovarian, colorectal, and breast cancers.

A hallmark of cancer is persistent new blood vessel formation, called angiogenesis. Angiopoietin-1 (Ang1) and Ang2 are members of a key pathway that regulate angiogenesis; Ang1 and Ang2 are secreted factors that bind to the endothelial cell—specific receptor tyrosine kinase Tie2. Ang1 is constitutively secreted by pericytes and stabilizes blood vessel integrity via the Tie2 receptor. Ang2 is released from endothelial cells only in response to stimulus (e.g. wound healing, tumor growth) and facilitates blood vessel sprouting and inhibits pericyte-endothelial cell interaction via Tie2 signaling. Studies have suggested that inhibition of Ang2 is more important than Ang1 for inhibiting angiogenesis, but in certain other studies, inhibition of Ang2 and Ang1 has shown benefits (Cascone et al., J Clin Onc (2012) 30(4):441).

An antibody against human Ang2, when dosed in combination with the VEGF blocker aflibercept, has been shown to inhibit tumor growth and to decrease tumor vascularity in mouse xenograft tumor models (REGN910 in Daly et al., Cancer Res (2013) 73(1):108 and H1H685P in WO2011014469). In Brown et al. (Mol Cancer Ther (2010) 9(1):145), mAb 3.19.3, a human Ang2 antibody, is reported to bind Ang1 with at least 500× less affinity than Ang2, while in Examples 4 and 9 of WO2006068953, 3.19.3 is disclosed by the applicants to have strong cross-reactivity to Ang1 with a $K_D$ for Ang2 of approximately 5 pM and a $K_D$ for Ang1 of approximately 30 pM. In a SW620 xenograft study, 3.19.3 was dosed in combination with DC101, a monoclonal antibody that binds murine VEGFR2.

There remains a need to provide alternative antibodies that inhibit the Ang/Tie2 angiogenesis pathway by binding human Ang2 with high affinity and neutralizing human Ang2. In particular, there remains a need to provide antibodies that bind human Ang2 with high affinity and neutralize human Ang2, but do not bind with high affinity or neutralize human Ang1.

Accordingly, an embodiment of the present invention provides an antibody, comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 3, and the HCVR has the amino acid sequence given in SEQ ID NO: 1.

Certain antibodies of the present invention bind human Ang-2 with a high affinity that is greater than human Ang2 antibodies known in the art. Furthermore, certain antibodies of the present invention demonstrate a positive response in tumor xenograft models, such as EL 1997 for triple negative breast cancer, SKOV3x.1 for ovarian cancer, and PC3 for prostate cancer, indicating potential as a cancer therapeutic. Additionally, certain antibodies of the invention selectively bind human Ang-2 over human Ang-1, and avoid potential off-target liabilities for human Ang1.

In a further embodiment, the present invention provides an antibody, wherein the LC has the amino acid sequence given in SEQ ID NO: 4, and the HC has the amino acid sequence given in SEQ ID NO: 2.

In a further embodiment, the present invention provides an antibody, comprising two light chains and two heavy chains, wherein each light chain has the amino acid sequence given in SEQ ID NO: 4, and each heavy chain has the amino acid sequence given in SEQ ID NO: 2.

In a further embodiment, the present invention provides an antibody, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In a further embodiment, the present invention provides an antibody, wherein the antibody is glycosylated.

In an embodiment, the present invention provides an antibody that binds human Ang2 (SEQ ID NO: 7), comprising a light chain (LC) and a heavy chain (HC), wherein the light chain comprises light chain complementarity determining regions LCDR1, LCDR2, and LCDR3 consisting of the amino acid sequences KASQDVYIAVA (SEQ ID NO: 8), YWASTRDT (SEQ ID NO: 9), and HQYSSYPPT (SEQ ID NO: 10), respectively, and wherein the heavy chain comprises heavy chain complementarity determining regions HCDR1, HCDR2, and HCDR3 consisting of the amino acid sequences GYSFTDYNMV (SEQ ID NO: 11), YIDPYNGGTGYNQKFEG (SEQ ID NO: 12), and ARTRDRYDVWYFDV (SEQ ID NO: 13), respectively.

In an embodiment, the present invention provides an antibody that binds human Ang2 (SEQ ID NO: 7), comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 3, and the HCVR has the amino acid sequence given in SEQ ID NO: 1.

In a further embodiment, the present invention provides an antibody that binds human Ang2 (SEQ ID NO: 7), wherein the LC has the amino acid sequence given in SEQ ID NO: 4, and the HC has the amino acid sequence given in SEQ ID NO: 2.

In a further embodiment, the present invention provides an antibody that binds human Ang2 (SEQ ID NO: 7), comprising two light chains and two heavy chains, wherein each light chain has the amino acid sequence given in SEQ ID NO: 4, and each heavy chain has the amino acid sequence given in SEQ ID NO: 2.

In a further embodiment, the present invention provides an antibody that binds human Ang2 (SEQ ID NO: 7), wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

In a further embodiment, the present invention provides an antibody that binds human Ang2 (SEQ ID NO: 7), wherein the antibody is glycosylated.

In a further embodiment, the present invention provides an antibody of the present invention that has a dissociation equilibrium constant, $K_D$, of less than about 150 pM for human Ang2. The antibody of the present invention is further characterized by a $k_{on}$ rate to human Ang2 of about $1 \times 10^6$ $M^{-1}sec^{-1}$. The antibody of the present invention is further characterized by a $k_{off}$ rate to human Ang2 of about $0.7 \times 10^{-4}$ $sec^{-1}$. The $K_D$, $k_{on}$, and $k_{off}$ values are established by binding kinetics at 37° C. as described in "Binding kinetics, affinity, and selectivity" in the Assays section.

The antibody of the present invention binds to human Ang2 with high affinity. For the purposes of the present disclosure, the term "high affinity" refers to a $K_D$ of less than about 150 pM for human Ang2. The $K_D$ values are established by binding kinetics at 37° C. as described in "Binding kinetics, affinity, and selectivity" in the Assays section.

In an embodiment, the present invention provides a mammalian cell, comprising a DNA molecule comprising a polynucleotide sequence encoding a polypeptide having an amino acid sequence of SEQ ID NO: 4 and a polynucleotide sequence encoding a polypeptide having an amino acid sequence of SEQ ID NO: 2, wherein the cell is capable of expressing an antibody comprising a light chain having an amino acid sequence of SEQ ID NO: 4 and a heavy chain having an amino acid sequence of SEQ ID NO: 2.

In an embodiment, the present invention provides a process for producing an antibody, comprising a light chain having an amino acid sequence of SEQ ID NO: 4 and a heavy chain having an amino acid sequence of SEQ ID NO: 2, comprising cultivating a mammalian cell of the present invention under conditions such that the antibody is expressed, and recovering the expressed antibody.

In an embodiment, the present invention provides an antibody produced by a process of the present invention.

In an embodiment, the present invention provides a pharmaceutical composition, comprising an antibody of the present invention, and an acceptable carrier, diluent, or excipient.

In an embodiment, the present invention provides a method of treating cancer, comprising administering to a patient in need thereof, an effective amount of an antibody of the present invention. In a further embodiment, the present invention provides a method of treating cancer, comprising administering to a patient in need thereof, an effective amount of an antibody of the present invention, wherein the cancer is breast cancer, ovarian cancer, gastric cancer, colorectal cancer, or hepatocellular carcinoma. In a further embodiment, these methods comprise the administration of an effective amount of the antibody of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab.

In a further embodiment, these methods comprise the administration of an effective amount of the compound of the present invention in simultaneous, separate, or sequential combination with one or more immuno-oncology agents selected from the group consisting of nivolumab, ipilimumab, pidilizumab, pembrolizumab, and durvalumab.

In an embodiment, the present invention provides a method of treating breast cancer, comprising administering to a patient in need thereof, an effective amount of an antibody of the present invention. In a further embodiment, these methods comprise the administration of an effective amount of the antibody of the present invention in simultaneous, separate, or sequential combination with one or more anti-tumor agents selected from the group consisting of ramucirumab, docetaxel, cyclophosphamide and doxorubicin, navelbine, eribulin, paclitaxel protein-bound particles for injectable suspension, ixabepilone, and capecitabine.

In an embodiment, the present invention provides a method of treating ovarian cancer, comprising administering to a patient in need thereof, an effective amount of an antibody of the present invention. In a further embodiment, these methods comprise the administration of an effective amount of the antibody of the present invention in simultaneous, separate, or sequential combination with one or more anti-tumor agents selected from the group consisting of ramucirumab, cisplatin, carboplatin, and liposomal doxorubicin.

In an embodiment, the present invention provides a method of treating gastric cancer, comprising administering to a patient in need thereof, an effective amount of an antibody of the present invention. In a further embodiment, these methods comprise the administration of an effective amount of the antibody of the present invention in simultaneous, separate, or sequential combination with ramucirumab.

In an embodiment, the present invention provides a method of treating hepatocellular carcinoma, comprising administering to a patient in need thereof, an effective amount of an antibody of the present invention. In a further embodiment, these methods comprise the administration of an effective amount of the antibody of the present invention in simultaneous, separate, or sequential combination with ramucirumab.

In an embodiment, the present invention provides a method of treating colorectal cancer, comprising administering to a patient in need thereof, an effective amount of an antibody of the present invention. In a further embodiment, these methods comprise the administration of an effective amount of the antibody of the present invention in simultaneous, separate, or sequential combination with one or more anti-tumor agents selected from the group consisting of ramucirumab, FOLFOX (leucovorin, fluorouracil, and oxaliplatin), FOLFIRI (leucovorin, fluorouracil, and irinotecan), and cetuximab.

In an embodiment, the present invention provides an antibody of the present invention, for use in therapy. In an embodiment, the present invention provides an antibody of the present invention, for use in the treatment of cancer. In a further embodiment, the present invention provides an antibody of the present invention, for use in the treatment of cancer, wherein the cancer is breast cancer, ovarian cancer, gastric cancer, colorectal cancer, or hepatocellular carcinoma. In a further embodiment, for use in the treatment of cancer, the antibody of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab.

In a further embodiment, for use in the treatment of cancer, the compound of the present invention in simultaneous, separate, or sequential combination with one or more immuno-oncology agents selected from the group consisting of nivolumab, ipilimumab, pidilizumab, pembrolizumab, and durvalumab.

In an embodiment, the present invention provides an antibody of the present invention, for use in the treatment of breast cancer. In a further embodiment, for use in the treatment of breast cancer, the antibody of the present invention in simultaneous, separate, or sequential combination with one or more anti-tumor agents selected from the group consisting of ramucirumab, docetaxel, cyclophosphamide and doxorubicin, navelbine, eribulin, paclitaxel protein-bound particles for injectable suspension, ixabepilone, and capecitabine.

In an embodiment, the present invention provides an antibody of the present invention, for use in the treatment of ovarian cancer. In a further embodiment, for use in the treatment of ovarian cancer, the antibody of the present invention in simultaneous, separate, or sequential combination with one or more anti-tumor agents selected from the group consisting of ramucirumab, cisplatin, carboplatin, and liposomal doxorubicin.

In an embodiment, the present invention provides an antibody of the present invention, for use in the treatment of gastric cancer. In a further embodiment, for use in the treatment of gastric cancer, the antibody of the present invention in simultaneous, separate, or sequential combination with ramucirumab.

In an embodiment, the present invention provides an antibody of the present invention, for use in the treatment of hepatocellular carcinoma. In a further embodiment, for use in the treatment of hepatocellular carcinoma, the antibody of the present invention in simultaneous, separate, or sequential combination with ramucirumab.

In an embodiment, the present invention provides an antibody of the present invention, for use in the treatment of colorectal cancer. In a further embodiment, for use in the treatment of colorectal cancer, the antibody of the present invention in simultaneous, separate, or sequential combination with one or more anti-tumor agents selected from the group consisting of ramucirumab, FOLFOX (leucovorin, fluorouracil, and oxaliplatin), FOLFIRI (leucovorin, fluorouracil, and irinotecan), and cetuximab.

In a further embodiment, the present invention provides the use of an antibody of the present invention for the manufacture of a medicament for the treatment of cancer. In a further embodiment, the present invention provides the use of an antibody of the present invention for the manufacture of a medicament for the treatment of cancer, wherein the cancer is breast cancer, ovarian cancer, gastric cancer, colorectal cancer, or hepatocellular carcinoma.

In a further embodiment, the present invention provides the use of an antibody of the present invention in simultaneous, separate, or sequential combination with one or more anti-tumor agents selected from the group consisting of cisplatin, carboplatin, liposomal doxorubicin, docetaxel, cyclophosphamide and doxorubicin, navelbine, eribulin, paclitaxel protein-bound particles for injectable suspension, ixabepilone, capecitabine, ramucirumab, FOLFOX (leucovorin, fluorouracil, and oxaliplatin), FOLFIRI (leucovorin, fluorouracil, and irinotecan), and cetuximab for the manufacture of a medicament for the treatment of cancer.

An antibody of the present invention is an engineered, non-naturally occurring polypeptide complex. A DNA molecule of the present invention is a non-naturally occurring DNA molecule that comprises a polynucleotide sequence encoding a polypeptide having the amino acid sequence of one of the polypeptides in an antibody of the present invention.

An antibody of the present invention is designed to have engineered CDRs and have some portions of the antibody (all or parts of the frameworks, hinge regions, and constant regions) to be of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. An antibody of the present invention may comprise framework, hinge, or constant regions derived from a fully human framework, hinge, or constant region containing one or more amino acid substitutions, deletions, or additions therein. Further, an antibody of the present invention is preferably substantially non-immunogenic in humans.

The antibody of the present invention is an IgG type antibody and has four amino acid chains (two "heavy" chains and two "light" chains) that are cross-linked via intra- and inter-chain disulfide bonds. Each heavy chain is comprised of an N-terminal HCVR and a heavy chain constant region ("HCCR"). Each light chain is comprised of a LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Optionally, the antibody of the present invention contains an Fc portion which is derived from human $IgG_4$ Fc region because of a reduced ability to engage Fc receptor-mediated inflammatory mechanisms or to activate complement resulting in reduced effector function.

Further, certain antibodies of the present invention contain an $IgG_4$-PAA Fc portion. The $IgG_4$-PAA Fc portion has a serine to proline mutation at position 229, a phenylalanine to alanine mutation at position 235, and a leucine to alanine mutation at position 236. The S229P mutation is a hinge mutation that prevents half-antibody formation (phenomenon of dynamic exchange of half-molecules in $IgG_4$ antibodies). The F235A and L236A mutations further reduce effector function of the already low human $IgG_4$ isotype.

The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1,CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures.

For the purposes of the present invention, a combination of the three methods is used to define CDRs. In the case of the light chain CDRs, the North CDR definitions are used.

In the case of HCDR1, a hybrid of the Kabat and Chothia CDR definitions is used. The Kabat definition of HCDR1 starts at the ninth residue after the first cysteine of the heavy chain and is typically five to seven residues in length, whereas the Chothia definition of HCDR1 starts at the fourth residue after this cysteine and is typically seven to nine residues in length. The HCDR1 of the antibody of the present invention is defined by the Chothia starting position and the Kabat end position. In the case of HCDR2, the Kabat CDR definition is used. In the case of HCDR3, a hybrid of the North, Kabat and Chothia CDR definitions is used. The Kabat definition of HCDR3 comprises residues 99-110 of the heavy chain (SEQ ID NO: 2 for the antibody of the present invention) and typically starts three residues after a cysteine. The Chothia definition of HCDR3 is the same as the Kabat definition. The North definition of HCDR3 comprises residues 97-110 of the heavy chain (SEQ ID NO: 2 for the antibody of the present invention) and typically starts immediately after the cysteine residue. The HCDR3 of the antibody of the present invention is defined by the North starting position and the Kabat/Chothia/North end position.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibody of the present invention may readily be produced in mammalian cells such as CHO, NS0, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, NY (1994).

In another embodiment of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

The antibody of the present invention, or pharmaceutical compositions comprising the same, may be administered by parenteral routes (e.g., subcutaneous and intravenous). An antibody of the present invention may be administered to a patient alone with pharmaceutically acceptable carriers, diluents, or excipients in single or multiple doses. Pharmaceutical compositions of the present invention can be prepared by methods well known in the art (e.g., *Remington: The Science and Practice of Pharmacy*, 19$^{th}$ ed. (1995), A. Gennaro et al., Mack Publishing Co.) and comprise an antibody, as disclosed herein, and one or more pharmaceutically acceptable carriers, diluents, or excipients.

The term "treating" (or "treat" or "treatment") refers to slowing, interrupting, arresting, alleviating, stopping, reducing, or reversing the progression or severity of an existing symptom, disorder, condition, or disease.

"Binds" as used herein in reference to the affinity of an antibody for human Ang2 is intended to mean, unless indicated otherwise, a $K_D$ of less than about $1\times10^{-8}$ M, preferably, less than about $1\times10^{-9}$ M as determined by common methods known in the art, including by use of a surface plasmon resonance (SPR) biosensor at 25° C. or 37° C. essentially as described herein. The term "selective" or "selectivity" used herein in reference to a compound of the present invention refers to a compound that binds a target, such as human Ang2, with a $K_D$ about 1000-, 500-, 200-, 100-, 50-, or about 10-fold lower than the compound binds other proteins, including member of the target family such as human Ang1, as measured by surface plasmon resonance at 25° C. or 37° C. Additionally, or alternatively, an Ang2 selective antibody of the present invention binds human Ang2 but does not bind or only minimally binds human Ang1 when assayed by the methods described in the Example herein below.

"Effective amount" means the amount of an antibody of the present invention or pharmaceutical composition comprising an antibody of the present invention that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects.

This invention is further illustrated by the following non-limiting example.

EXAMPLE 1: ANTIBODY EXPRESSION AND PURIFICATION

The polypeptides of the variable regions of the heavy chain and light chain, the complete heavy chain and light chain amino acid sequences of Antibody A, and the nucleotide sequences encoding the same, are listed below in the section entitled "Amino Acid and Nucleotide Sequences." In addition, the SEQ ID NOs for the light chain, heavy chain, light chain variable region, and heavy chain variable region of Antibody A are shown in Table 1.

The antibodies of the present invention, including, but not limited to, Antibody A can be made and purified essentially as follows. An appropriate host cell, such as HEK 293 or CHO, can be either transiently or stably transfected with an expression system for secreting antibodies using an optimal predetermined HC:LC vector ratio (such as 1:3 or 1:2) or a single vector system encoding both HC and LC. Clarified media, into which the antibody has been secreted, may be purified using any of many commonly-used techniques. For example, the medium may be conveniently applied to a MabSelect column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer pH 7 to 10 mM sodium citrate buffer pH 3.0, or phosphate buffered saline pH 7.4 to 100 mM glycine buffer pH 3.0). Antibody fractions may be detected, such as by SDS-PAGE, and then may be pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is greater than 95%. The product may be immediately frozen at −70° C. or may be lyophilized.

TABLE 1

SEQ ID NOs

| | Antibody A |
|---|---|
| HCVR | 1 |
| LCVR | 3 |
| Heavy chain | 2 |
| Light chain | 4 |

Assays
Binding Kinetics, Affinity, and Selectivity

The binding kinetics, affinity, and selectivity for multiple species of soluble Ang2 such as human, cynomolgous, mouse, rabbit and dog, may be determined for antibodies of the present invention at 25° C. or 37° C. by use of a surface plasmon resonance (SPR) biosensor such as a BIAcore® 2000, BIAcore® 3000, or a BIAcore® T100 (GE Healthcare) according to methods known in the art.

Human Ang2 may be purchased from R&D Systems. Protein A surface for capture of antibodies may be prepared using the following methods Immobilization of soluble Protein A (Calbiochem, Cat: 539202) on a CM4 (Biacore #BR-1005-34) or CM5 (Biacore #BR-1000-99) may be prepared using EDC/NHS amine coupling method (Biacore #BR-1000-50). Briefly, the surfaces of all four flow cells may be activated by injecting a 1:1 mixture of EDC/NHS for seven minutes at 5 µl/min or 10 µL/min. After which, soluble protein A may be diluted in 10 mM acetate buffer, pH 4.5, and immobilized for seven minutes onto flow cell (Fc) 2, 3 or 4 at a flow rate of 5 µL/min or 10 µL/min. Un-reacted sites still remaining on the chip surface may be blocked with a seven minute injection of ethanolamine at 5 µL/min or 10 µL/min. Running buffer may be HBS-EP+ (Biacore #BR-1006-69). Antibody samples may be prepared at 1 µg/mL or 2 µg/mL by dilution into running buffer. Discrete concentrations of Ang2 ligands ranging from 200 nM to 3.1 nM may be prepared using a two-fold serial dilution into running buffer. Each analysis cycle may consist of a series of five separate steps: (1) capture of antibody onto separate flow cells (Fc2, Fc3, and Fc4), (2) injection (using kinject) of 250 µL (300-second surface contact time) of discrete concentrations of Ang2 over all Fc at 50 µL/min, (3) return to buffer flow for 20 minutes to monitor dissociation phase, (4) regeneration of chip surfaces with a 10 µL (30-second contact time) injection of 10 mM glycine, pH 1.5, (5) equilibration of chip surface with a 15 µL (45-second contact time) injection of HBS-EP+ running buffer. Resultant data may be processed using standard double-referencing and fit to a 1:1 binding model using Biacore 2000 Evaluation software, version 4.1, to determine the association rate ($k_{on}$, $M^{-1}s^{-1}$ units), dissociation rate ($k_{off}$, $s^{-1}$ units). Calculation of the equilibrium dissociation constant ($K_D$) may be calculated from the following relationship, $K_D = k_{off}/k_{on}$, and is presented in molar units.

H1H685P-293HEK is a human IgG1 Ang2 antibody expressed in 293 HEK cells that utilizes an HCVR sequence (SEQ ID NO: 18 from WO2011014469) and a LCVR sequence (SEQ ID NO: 20 from WO2011014469). 3.19.3-293HEK is a human IgG1 antibody expressed in 293 HEK cells that binds Ang2 and utilizes the 3.19.3 HCVR sequence (SEQ ID NO: 2 from WO2009097325) and the MEDI1 LCVR sequence (SEQ ID NO: 3 from WO2009097325).

In experiments performed essentially as described in this assay, Antibody A binds to human Ang2 with a $K_D$ approximately 4× and 8× lower than H1H685P-293HEK and 3.19.3-293HEK, respectively (Table 2).

In experiments performed essentially as described in this assay, Antibody A binds human, cynomolgus, mouse, rabbit and dog Ang2 with affinities of 80, 107, 109, 210 and 140 pM, respectively (Table 3).

TABLE 2

Biacore SPR Parameters for hAng2 Binding (25° C.)

| | $k_{on}$ ($10^5$ 1/Ms) | $k_{off}$ ($10^{-4}$ 1/s) | $K_D$ (pM) |
|---|---|---|---|
| H1H685P-293HEK | 1.06 | 0.20 | 185 |
| Antibody A | 7.47 | 0.28 | 38 |
| 3.19.3-293HEK | 2.44 | 0.80 | 330 |

TABLE 3

Antibody A Biacore SPR Parameters for Ang2 Binding (37° C., n = 3)

| | $k_{on}$ (1/Ms) | $k_{off}$ (1/s) | $K_D$ (pM) |
|---|---|---|---|
| human Ang2 | 1.0 (±0.4) × $10^6$ | 0.7 (±0.2) × $10^{-4}$ | 80 ± 50 |
| cyno Ang2 | 2.7 (±0.2) × $10^6$ | 2.9 (±0.1) × $10^{-4}$ | 107 ± 6 |
| mouse Ang2 | 1.0 (±0.2) × $10^6$ | 1.1 (±0.1) × $10^{-4}$ | 109 ± 9 |
| rabbit Ang2 | 7.3 (±1.9) × $10^5$ | 1.5 (±0.1) × $10^{-4}$ | 210 ± 40 |
| dog Ang2 | 7.9 (±3.2) × $10^5$ | 1.1 (±0.4) × $10^{-4}$ | 140 ± 10 |
| rat Ang2 | 1.2 (±0.04) × $10^6$ | 2.0 (±0.2) × $10^{-4}$ | 180 ± 20 |

Affinity Measurement with Kinexa

A KinExA 3200 instrument (Sapidyne Inst. Inc.) may be used to measure binding kinetics. Briefly, human Ang2 may be covalently coupled to sepharose beads and the binding of free Mab to the beads may be detected on the KinExA 3200. To measure $K_D$, individual tubes containing Mab (1 pM, 2 pM, or 5 pM) with decreasing serially diluted human Ang2 may be incubated for a few days at 25° C. in PBS containing 1 mg/ml BSA. After the incubation, free Mab in each equilibrated sample may be determined. $K_d$ values may be determined using N-curve analysis with KinExA software.

In experiments performed essentially as described in this assay, Antibody A binds to human Ang2 with a $K_D$ about 8× lower than H1H685P-293HEK (Table 4).

TABLE 4

| Antibody | $K_D$ (pM) | 95% confidence interval |
|---|---|---|
| Antibody A | 0.11 pM | <0.0004 pM-0.56 pM |
| H1H685P-293HEK | 0.87 pM | 0.15 pM-2.2 pM |

Antibody A Inhibits Interaction of Human Ang2 to Human Tie2 via Solid Phase ELISA Assay The blocking of human Ang2 binding to its receptor human Tie2 by an antibody of the present invention may be measured in a solid phase in vitro ELISA assay.

For the assay, high binding 96-well ELISA plates (Costar #2592) may be coated with 4 µg/ml (in 100 µl) recombinant human Tie2-Fc (R&D Systems #313-TI), overnight at room temperature. The plates may be washed 3× with TBST (Tris buffered saline containing 0.05% Tween 20) and then may be blocked with 300 µl/well of blocking buffer (0.5% BSA/D-PBS) (BSA: Jackson ImmunoResearch #001-000-162; IgG-free, protease-free) for 1-2 hours at room temperature on an orbital shaker. During the blocking step, in separate polypropylene mutiwell plates, 75 µl of 2× test antibodies (serially diluted 1:3 in blocking buffer) may be added with 75 µl of 2× biotinylated human Ang2 (R&D Systems #BT623) (also diluted in blocking buffer). The antibody/biotinylated Ang2 mixtures may then be incubated for 1 hour at 37° C. (final biotinylated Ang2 concentration was 100 ng/ml). The blocking solution may be removed from the Tie2-Fc coated ELISA plates, after which 50 µl per well of the antibody/biotinylated Ang2 mixtures may be added (in duplicate wells). The plates may then be incubated for 2 hours at room temperature, covered with plate sealers, on an orbital shaker. Plates may then be washed 3×, after which 100 µl per well of streptavidin-HRP (R&D Systems #DY998, may be diluted 1:200 in blocking buffer) may be added. Plates may then be incubated for 45 minutes at room temperature, covered with plate sealers, on an orbital shaker. Plates may then be washed again 3×.

Plates may then be developed by adding 100 µl per well of One Component TMB substrate (may be warmed to room temperature) (Surmodics/BioFX Labs #TMBW-1000-01). Development may be allowed to progress for 10 minutes at room temperature (plates may be covered with aluminum foil). Development may be stopped with 100 µl per well of acid stop solution (TMB stop solution, Surmodics/BioFX Labs #LSTP-1000-01). Plates may be mixed on an orbital shaker after which they may be read at 450 nm on an ELISA reader (Molecular Devices SpectraMax 190), using SOFTmax PRO 5.4.1 software (Molecular Devices Corp.). The A450 values reflect the amount of biotinylated Ang2 that remained bound to Tie-2-Fc. Reduction of A450 values reflected blocking of biotinylated Ang2 binding to Tie-2-Fc.

IC50 values for inhibition of Ang2 binding to Tie-2 may be calculated with GraphPad Prism 6, using Log-transformed X values. Nonlinear regression (curve fit) analysis (sigmoidal dose response, variable slope) may be performed on the log-transformed data to obtain IC50 values. If an experiment is performed more than once, the geometric mean IC50 value (and 95% confidence interval) between experiments may be calculated.

In experiments performed essentially as described in this assay, Antibody A specifically blocked binding of Ang2 to Tie-2 in a dose-dependent manner, resulting in geometric mean IC50 value (n=2) of 0.027 nM (95% confidence interval 0.00089-0.8029 nM). Antibody A and H1H685P-293HEK had comparable neutralization IC50 values.

Neutralization of Ang2 Induced Phosphorylation of Tie-2 but not Ang1 Mediated Phosphorylation.

The in vitro cell-based inhibition of human Tie-2 by an antibody of the present invention may be measured in a cell-based assay where Ang1 and Ang2 bind to and induce human Tie-2 phosphorylation in a dose-dependent manner. The in vitro cell-based assay may be used to evaluate the ability of Antibody A to selectively neutralize Ang2 and not Ang1 mediated phosphorylation of the Tie-2 receptor in a dose-dependent manner. An Ang2 antibody, an Ang1/2 cross-reactive antibody, and a control human IgG4 PAA isotype antibody may be included as positive and negative controls respectively.

The CHO-Tie-2 cell line may be generated by stable transfection of a full-length human Tie-2 receptor (with a 3×FLAG tag at the C-terminus). CHO-Tie-2 cells may be maintained in complete medium of Hams F-12 (CellGro/Mediatech #10-080-CV), 10% heat inactivated FBS (Life Technologies/Invitrogen #10082-147), 1× antibiotic-antimycotic (Life Technologies/Invitrogen #15240-062), 1.25 mg/ml G418 (Corning Cellgro #30-234-CI), 10 µg/ml puromycin (Calbiochem #540411), and 0.078% sodium bicarbonate (Thermo Hyclone #SH30033.01).

For the assay, CHO-Tie-2 cells may be resuspended to 10,000 cells per well (in 100 µl growth medium), into the inner 60 wells of poly-lysine coated 96-well plates (BD Biocoat #356640). 200 µl of D-PBS may be placed into the edge wells to reduce evaporation. Cells may be incubated overnight at 37° C., 95% RH, 5% $CO_2$. The next day, cells may be washed once and medium may be replaced with 100 µl serum-free growth medium containing 0.1% BSA (Sigma #A7979, low endotoxin). Cells may then be starved for 7.5 to 24 hours in serum-free medium at 37° C., 95% RH, 5% $CO_2$. During the starvation period, antibodies (at 6× the final concentrations) may be serially diluted 1:2 in polypropylene plates in serum-free growth medium containing 0.1% BSA. Human Ang2 (R&D Systems #623-AN, reconstituted in D-PBS/0.1% BSA) and human Ang1 (R&D Systems #923-AN, reconstituted in D-PBS/0.1% BSA) may also be diluted to 6× the final concentration in serum-free growth medium containing 0.1% BSA. Antibodies and the Ang2 or Ang1 ligand may then be mixed at a 1:1 ratio in polypropylene plates and may be incubated for 1 hour at 37° C. The antibody/ligand mixtures may then be added at 50 µl per well to the cells (in triplicate wells per treatment) and may be incubated for 13 minutes to 21 hours at 37° C., 95% RH, 5% $CO_2$. The final concentration range of antibody may be 0.0625-283 nM, and the final concentration of human Ang2 and Ang1 may be 0.3 µg/ml (approx. 6 nM) and 0.5 µg/ml (approx. 8.9 nM), respectively. After the incubation time, medium may be quickly and fully removed from the cells, and cells may be lysed in 60 µl per well of cold 1× Tris Lysis Buffer (Meso Scale Discovery #R60TX; 150 mM NaCl, 20 mM Tris pH 7.5, 1 mM EDTA, 1 mM EGTA, 1% Triton X-100) which may contain freshly added protease and phosphatase inhibitors (1× protease inhibitor cocktail, Sigma #P8340; 1× phosphatase inhibitor cocktail 2, Sigma #P5726; 1× phosphatase inhibitor cocktail 3, Sigma #P0044; 1 mM final activated sodium orthovanadate (EMD Chemicals #567540)). Plates may then be placed on ice for 10 minutes, after which they may be placed on an orbital shaker at low speed for 25 minutes at 4° C. The plates may then be sealed and frozen at −80° C.

The day before analysis for phospho-Tie-2 (with a human phospho-Tie-2 DuoSet ELISA kit from R&D Systems, #DYC2720), high binding ELISA plates (Greiner BioOne, #655081) may be coated overnight at 4° C. with 4 µg/ml mouse anti-human total Tie-2 capture antibody in 1×ELISA coating buffer (Surmodics/BioFX Labs #COAT-1000-01).

The day of phospho-Tie-2 measurement, plates containing lysates may be thawed on ice. The coated ELISA plates may be washed with wash buffer (1×TBST containing 0.05% Tween 20) and blocked with 300 µl per well of blocking buffer (1% BSA (Jackson ImmunoResearch #001-000-162; IgG-free, protease-free), 0.01% sodium azide) for a minimum of 1 hour at room temperature on an orbital shaker (while covered with plate sealers). During blocking, lysates may be diluted 1:5 or 1:10 in polypropylene plates in cold lysis buffer containing protease and phosphatase inhibitors. ELISA plates may be blocked and washed 4×, and 100 µl per well of diluted lysates (or phospho-Tie-2 ELISA standards) may be added and incubated for 2 hours at room temperature, covered with sealers, on an orbital shaker. Plates may be washed 4× and 100 µl per well of HRP conjugated mouse anti-phospho tyrosine (diluted as recommended on the vial, in TBST/0.1% BSA) may be added. Plates may then be covered with sealers, and incubated for 2 hours at room temperature on an orbital shaker. Plates may then be washed 6× and removal of liquid from the wells may be ensured. Plates may then be developed by adding 100 µl per well of One Component TMB substrate (Surmodics/BioFX Labs #TMBW-1000-01). Plates may be allowed to develop for 20 or 30 minutes at room temperature covered with aluminum foil. Development may be stopped with 100 µl per well of acid stop solution (TMB stop solution, Surmodics/BioFX Labs #LSTP-1000-01). Plates may then be mixed on an orbital shaker. The ELISA plates may be read at 450 nm on an ELISA reader (Molecular Devices SpectraMax 190), using SOFTmax PRO 5.4.1 software (Molecular Devices Corp.). Phospho-Tie-2 values for the samples may be obtained from the standard curve (4-parameter logistic fit), and multiplied by the dilution factor of 5 or 10. Percent inhibition may be calculated by the following formula: (pTie2 value of treatment-mean pTie2 value of Ang2 alone treatment)/(mean medium alone pTie2 value—mean pTie2 value of Ang2 alone treatment)*100.

IC50 values for inhibition of Ang2 induced phospho-Tie-2 may be calculated with GraphPad Prism 4, using Log-transformed X values. Nonlinear regression (curve fit) analysis (sigmoidal dose response, variable slope) may be performed on the log-transformed data to obtain $IC_{50}$ values. If an experiment was performed more than once, the geometric mean $IC_{50}$ value (and 95% confidence interval) between experiments may be calculated.

In experiments performed essentially as described in this assay, Antibody A dose-dependently neutralized human Ang2 induced phospho-Tie-2 in CHO-Tie-2 cells with an IC50 of 0.773 nM (95% confidence interval 0.412-1.45 nM) (n=3). Furthermore, Antibody A did not neutralize human Ang1 induced phospho-Tie-2 in CHO-Tie-2 cells when compared to the anti-Ang1/2 cross-reactive antibody 3.19.3-293HEK. Antibody A and H1H685P-293HEK had comparable Ang2 neutralization IC50 values.

Repression of Ang2 Induced Blood Vessel Development

The in vivo repression of physiological angiogenesis by an Ang2 antibody may be measured in a model of blood vessel development in the mouse retina. The aforementioned assay may be used to study the ability of antibodies of the present invention to repress physiological angiogenesis in the mouse retina.

For this assay, the day of mouse pup delivery by the pregnant females may be marked P0 (postnatal day 0). Following delivery, at days two and four (P2 and P4) pups may be injected with vehicle control (PBS) or 10 mg/kg of Antibody A. At P5 mice may be sacrificed and eyes may be harvested and may be fixed in formalin for 5 hours and may be washed with PBS.

Retinas may then be dissected, and may be stained with anti-CD31 diluted at 1:200 (BD Pharmingen; clone MEC 13.3; Catalog 553370), and anti-SMA-FTIC diluted at 1:200 (Sigma; Clone1A4 Catalog F3777). For the anti-CD31 treated retinas an anti-Rat Alexa-647 diluted at 1:400 (Jackson Immuno Research; Catalog 712-606-153) may be used as a secondary antibody. Acquisition of the retinas may be done by using Nikon Ti, and quantifications of vascular progression, number of sprouting tip cells, and vascular density of remodeling plexus may be performed by using FIJI software. High magnification images may be acquired using a confocal Nikon A1.

In experiments performed essentially as described in this assay, Antibody A repressed vascular progression, reduced both the number of endothelial tip cells and vascular density, as well as increased pericyte coverage similarly at 3 mg/kg, 10 mg/kg and 30 mg/kg when compared to the PBS control group. This data was statistically significant with p<0.0001 for all treatment groups when compared to the PBS control group (Table 5).

TABLE 5

| Parameters | Vehicle (PBS) | Antibody A (30 mg/kg) | Antibody A (10 mg/kg) | Antibody A (3 mg/kg) |
|---|---|---|---|---|
| Vascular progression | | | | |
| Mean (%) | 100 | 59.91 | 59.76 | 67.73 |
| Std. Error of Mean | 5.046 | 3.848 | 2.524 | 2.463 |
| P value (Vehicle vs. Compounds) (Dunnett's test) | | <0.0001 | <0.0001 | <0.0001 |
| P value (30 vs. 10 and 3 mg/kg) (Dunnett's test) | | | >0.9999 | 0.2457 |
| P value (10 vs. 3 mg/kg) (Dunnett's test) | | | | 0.2892 |
| Number of tip cells | | | | |
| Mean (%) | 100 | 41.82 | 47.79 | 52.25 |
| Std. Error of Mean | 6.181 | 3.25 | 4.647 | 3.474 |
| P value (Vehicle vs. Compounds) (Dunnett's test) | | <0.0001 | <0.0001 | <0.0001 |
| P value (10 and 3 mg/kg) (Dunnett's test) | | | 0.6685 | 0.1899 |
| P value (10 vs. 3 mg/kg) (Dunnett's test) | | | | 0.8290 |
| Vascular density | | | | |
| Mean (%) | 100 | 58.51 | 55.97 | 60.06 |
| Std. Error of Mean | 4.48 | 2.685 | 3.569 | 3.056 |
| P value (Vehicle vs. Compounds) (Dunnett's test) | | <0.0001 | <0.0001 | <0.0001 |
| P value (10 and 3 mg/kg) (Dunnett's test) | | | 0.9105 | 0.9735 |
| P value (10 vs. 3 mg/kg) (Dunnett's test) | | | | 0.7396 |

In Vivo Anti-Angiogenic Effects of Antibody A in PC3 Prostate Cancer Xenograft Model The anti-angiogenic effect of Ang2 antibodies and Ang2 antibodies in combination with VEGFR2 antibodies may be evaluated in a PC3 prostate cancer xenograft model.

Mice bearing PC3 xenograft tumors at approximately 250 mm³ volume, randomized at 10 mice/group, may be treated with control IgG1, DC101 (an anti-VEGFR2 murine antibody), Antibody A, DC101+Antibody A for 6 days (2QW; 20 mg/kg). After six days, tumors may be collected, fixed and sectioned. The sectioned tumors may be stained for CD105 and the total vessel area may be determined.

In experiments performed essentially as described, when compared to the control IgG1 group, the total vessel area was reduced by 65% in the DC101 treatment group, 69% in the Antibody A treatment group, and 84% in the combination treatment group. When compared to the IgG1 control group, these results were statistically significant with a p<0.0001 for all the treatment groups.

Antibody A and Anti-VEGFR2 Antibody Inhibits in vivo Tumor Growth

The efficacy of the antibodies of the present invention may be measured via in vivo xenograft models. The anti-tumor efficacy of DC101 (an anti-VEGFR2 murine antibody), Antibody A and its combination may be assessed in the subcutaneous triple negative patient derived breast cancer model (EL1997) and the subcutaneous ovarian xenograft model (SKOV3x.1). Mice bearing tumors may be treated with antibodies diluted in PBS, on a twice weekly basis via intra-peritoneal injection. Tumor growth may be determined by three dimensional caliper measurements of tumor volumes twice weekly during the course of treatment.

EL1997 Triple Negative Breast Patient Derived Xenografts:

Immuno-deficient mice bearing EL1997 triple negative breast patient derived xenografts (TNBC PDX) at approximately 350 mm³ volume randomized at n=7 mice/group may be treated with vehicle control, DC101 monotherapy at 20 mg/kg, Antibody A monotherapy at 20 mg/kg, Cyclophosphamide and Doxorubicin combination at 100 mg/kg and 10 mg/kg respectively, DC101 and Antibody A combination or Cyclophosphamide, Doxorubicin, DC101 and Antibody A combination dosed at the respective monotherapy concentrations. Treatments may be administered twice a week for 4 consecutive weeks.

In experiments performed essentially as described, DC101 and Antibody A monotherapy treatment groups exhibited a % T/C (change in tumor volume) of 35.2% and 56.7%, respectively. The combination of the two antibodies, DC101 and Antibody A resulted in a % T/C of 19.9%. Furthermore, the combination of Cyclophosphamide, Doxorubicin, DC101 and Antibody A resulted in a % T/C of 0.4%, with a statistically significant (p=0.0019) reduction in tumor volume when compared to the combination of DC101 and Antibody A. The combination treatment of the chemotherapeutic agents alone, Cyclophosphamide and Doxorubicin resulted in a % TC of 32%. These results indicate that the monotherapy treatment with DC101 or Antibody A is efficacious, and has potential for greater efficacy in combination; which is further enhanced with the addition of chemotherapeutic agents.

SKOV3x.1 Ovarian Xenografts:

Immuno-deficient mice bearing SKOV3x.1 ovarian xenografts at approximately 350 mm³ volume, randomized at n=10 mice/group, may be treated with vehicle control, Antibody A monotherapy at 3, 10 or 30 mg/kg, Paclitaxel monotherapy at 25 mg/kg or the combination of Paclitaxel and Antibody A at 25 mg/kg and 10 mg/kg respectively. Treatments may be administered twice a week for 4 weeks.

In experiments performed essentially as described, the results showed a % T/C values of 39.1, 32.5 and 27.3 for 3, 10 and 30 mg/kg doses of Antibody A respectively and % T/C of 20.3 for 25 mg/kg paclitaxel monotherapy with p values of <0.001 compared with the control. The combination of 25 mg/kg Paclitaxel and 10 mg/kg Antibody A enhanced the efficacy of the two monotherapies, showing a % T/C of 7.1% when compared to the vehicle control group.

SKOV3x.1 Ovarian Xenografts:

Immuno-deficient mice bearing SKOV3x.1 ovarian xenografts at approximately 250 mm³ volume, randomized at n=10 mice/group, may be treated with vehicle control, DC101 monotherapy at 20 mg/kg, Paclitaxel monotherapy at 25 mg/kg, DC101 and Antibody A combination at 25 mg/kg each, or Paclitaxel, DC101 and Antibody A combination dosed at the respective monotherapy concentrations. Treatments may be administered twice a week for 4 weeks.

In experiments performed essentially as described, monotherapy treatment of DC101 resulted in a % T/C of 9.6%, whereas the combination of the two antibodies, DC101 and Antibody A, resulted in an improved % T/C of 0.1% when compared to the vehicle control group. The combination of Paclitaxel, DC101 and Antibody A resulted in tumor regressions of about −33% compared to a % T/C of 17.8% for the Paclitaxel monotherapy. These results indicate in the xenograft model that VEGFR2 inhibition with DC101 has potential for greater efficacy in combination with Antibody A. The benefit of this combination is further enhanced with the addition of a chemotherapeutic agent leading to statistically significant regressions in tumor volumes.

Amino Acid and Nucleotide Sequences

SEQ ID NO: 1 (HCVR of Antibody A)
QVQLVQSGAEVKKPGASVKVSCKASGYSFTDYNMVWVRQAPGQGLEWMGYI
DPYNGGTGYNQKFEGRVTMTTDTSTSTAYMELRSLRSDDTAVYYCARTRDR
YDVWYFDVWGQGTLVTVSS SEQ ID NO: 2 (HC of Antibody A)
QVQLVQSGAEVKKPGASVKVSCKASGYSFTDYNMVWVRQAPGQGLEWMGYI
DPYNGGTGYNQKFEGRVTMTTDTSTSTAYMELRSLRSDDTAVYYCARTRDR
YDVWYFDVWGQGTLVTVSSASTKGPSVFPLAPCSRSTSESTAALGCLVKDY
FPEPVTVSWNSGALTSGVHTFPAVLQSSGLYSLSSVVTVPSSSLGTKTYTC
NVDHKPSNTKVDKRVESKYGPPCPPCPAPEAAGGPSVFLFPPKPKDTLMIS
RTPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQE
EMTKNQVSLTCLVKGFYPSDIAVEWESNGQPENNYKTTPPVLDSDGSFFLY
SRLTVDKSRWQEGNVFSCSVMHEALHNHYTQKSLSLSLG SEQ ID NO: 3 (LCVR of Antibody A)
DIQMTQSPSSVSASVGDRVTITCKASQDVYIAVAWYQQKPGKAPKLLIYWA
STRDTGVPSRFSGSGSGTDFTLTISSLQPEDFATYYCHQYSSYPPTFGGGT
KVEIK SEQ ID NO: 4 (LC of Antibody A)
DIQMTQSPSSVSASVGDRVTITCKASQDVYIAVAWYQQKPGKAPKLLIYWA
STRDTGVPSRFSGSGSGTDFTLTISSLQPEDFATYYCHQYSSYPPTFGGGT
KVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSP
VTKSFNRGEC

| Amino Acid and Nucleotide Sequences |
|---|
| SEQ ID NO: 5 (DNA of LC of Antibody A)<br>GACATCCAGATGACCCAGTCTCCATCTTCCGTGTCTGCATCTGTAGGAGAC<br>AGAGTCACCATCACTTGTAAGGCCAGTCAGGATGTGTATATTGCTGTAGCC<br>TGGTATCAGCAGAAACCAGGGAAAGCCCCTAAGCTCCTGATCTATTGGGCA<br>TCCACCCGGGACACTGGGGTCCCATCAAGGTTCAGCGGCAGTGGATCTGGG<br>ACAGATTTCACTCTCACCATCAGCAGCCTGCAGCCTGAAGATTTTGCAACT<br>TACTATTGTCACCAATATAGCAGCTATCCTCCTACGTTCGGCGGAGGGACC<br>AAGGTGGAGATCAAACGGACTGTGGCTGCACCATCTGTCTTCATCTTCCCG<br>CCATCTGATGAGCAGTTGAAATCTGGAACTGCCTCTGTTGTGTGCCTGCTG<br>AATAACTTCTATCCCAGAGAGGCCAAAGTACAGTGGAAGGTGGATAACGCC<br>CTCCAATCGGGTAACTCCCAGGAGAGTGTCACAGAGCAGGACAGCAAGGAC<br>AGCACCTACAGCCTCAGCAGCACCCTGACGCTGAGCAAAGCAGACTACGAG<br>AAACACAAAGTCTACGCCTGCGAAGTCACCCATCAGGGCCTGAGCTCGCCC<br>GTCACAAAGAGCTTCAACAGGGGAGAGTGC<br>SEQ ID NO: 6 (DNA of HC of Antibody A)<br>CAGGTTCAGCTGGTGCAGTCTGGAGCTGAGGTGAAGAAGCCTGGGGCCTCA<br>GTGAAGGTCTCCTGCAAGGCTTCTGGTTACTCATTCACTGACTACAACATG<br>GTGTGGGTGCGACAGGCCCCTGGACAAGGGCTTGAGTGGATGGGATATATT<br>GATCCTTACAATGGTGGTACTGGCTACAACCAGAAGTTCGAGGGCAGAGTC<br>ACCATGACCACAGACACATCCACGAGCACAGCCTACATGGAGCTGAGGAGC<br>CTGAGATCTGACGACACGGCCGTGTATTACTGTGCGAGAACGAGGGATAGG<br>TACGACGTCTGGTACTTCGATGTCTGGGGCCAGGGAACCCTGGTCACCGTC<br>TCCTCAGCCTCCACCAAGGGCCCATCGGTCTTCCCGCTAGCGCCCTGCTCC<br>AGGAGCACCTCCGAGAGCACAGCCGCCCTGGGCTGCCTGGTCAAGGACTAC<br>TTCCCCGAACCGGTGACGGTGTCGTGGAACTCAGGCGCCCTGACCAGCGGC<br>GTGCACACCTTCCCGGCTGTCCTACAGTCCTCAGGACTCTACTCCCTCAGC<br>AGCGTGGTGACCGTGCCCTCCAGCAGCTTGGGCACGAAGACCTACACCTGC<br>AACGTAGATCACAAGCCCAGCAACACCAAGGTGGACAAGAGAGTTGAGTCC<br>AAATATGGTCCCCCATGCCCACCCTGCCCAGCACCTGAGGCCGCCGGGGGA<br>CCATCAGTCTTCCTGTTCCCCCCAAAACCCAAGGACACTCTCATGATCTCC<br>CGGACCCCTGAGGTCACGTGCGTGGTGGTGGACGTGAGCCAGGAAGACCCC<br>GAGGTCCAGTTCAACTGGTACGTGGATGGCGTGGAGGTGCATAATGCCAAG<br>ACAAAGCCGCGGGAGGAGCAGTTCAACAGCACGTACCGTGTGGTCAGCGTC<br>CTCACCGTCCTGCACCAGGACTGGCTGAACGGCAAGGAGTACAAGTGCAAG<br>GTCTCCAACAAAGGCCTCCCGTCCTCCATCGAGAAAACCATCTCCAAAGCC<br>AAAGGGCAGCCCCGAGAGCCACAGGTGTACACCCTGCCCCCATCCCAGGAG<br>GAGATGACCAAGAACCAGGTCAGCCTGACCTGCCTGGTCAAAGGCTTCTAC<br>CCCAGCGACATCGCCGTGGAGTGGGAAAGCAATGGGCAGCCGGAGAACAAC<br>TACAAGACCACGCCTCCCGTGCTGGACTCCGACGGCTCCTTCTTCCTCTAC<br>AGCAGGCTAACCGTGGACAAGAGCAGGTGGCAGGAGGGGAATGTCTTCTCA<br>TGCTCCGTGATGCATGAGGCTCTGCACAACCACTACACACAGAAGAGCCTC<br>TCCCTGTCTCTGGGT<br>SEQ ID NO: 7 (human Ang2)<br>YNNFRKSMDSIGKKQYQVQHGSCSYTFLLPEMDNCRSSSSPYVSNAVQRDA<br>PLEYDDSVQRLQVLENIMENNTQWLMKLENYIQDNMKKEMVEIQQNAVQNQ<br>TAVMIEIGTNLLNQTAEQTRKLTDVEAQVLNQTTRLELQLLEHSLSTNKLE<br>KQILDQTSEINKLQDKNSFLEKKVLAMEDKHIIQLQSIKEEKDQLQVLVSK<br>QNSIIEELEKKIVTATVNNSVLQKQQHDLMETVNNLLTMMSTSNSAKDPTV<br>AKEEQISFRDCAEVFKSGHTTNGIYTLTFPNSTEEIKAYCDMEAGGGGWTH<br>QRREDGSVDFQRTWKEYKVGFGNPSGEYWLGNEFVSQLTNQQRYVLKIHLK<br>DWEGNEAYSLYEHFYLSSEELNYRIHLKGLTGTAGKISSISQPGNDFSTKD<br>GDNDKCICKCSQMLTGGWWFDACGPSNLNGMYYPQRQNTNKFNGIKWYYWK<br>GSGYSLKATTMMIRPADF<br>SEQ ID NO: 8 (LCDR1 of Antibody A)<br>KASQDVYIAVA<br>SEQ ID NO: 9 (LCDR2 of Antibody A)<br>YWASTRDT<br>SEQ ID NO: 10 (LCDR3 of Antibody A)<br>HQYSSYPPT<br>SEQ ID NO: 11 (HCDR1 of Antibody A)<br>GYSFTDYNMV<br>SEQ ID NO: 12 (HCDR2 of Antibody A)<br>YIDPYNGGTGYNQKFEG<br>SEQ ID NO: 13 (HCDR3 of Antibody A)<br>ARTRDRYDVWYFDV |

We claim:

1. An antibody that binds human Ang2 (SEQ ID NO: 7), comprising a light chain (LC) and a heavy chain (HC), wherein the light chain comprises light chain complementarity determining regions LCDR1, LCDR2, and LCDR3 consisting of the amino acid sequences KASQDVYIAVA (SEQ ID NO: 8), YWASTRDT (SEQ ID NO: 9), and HQYSSYPPT (SEQ ID NO: 10), respectively, and wherein the heavy chain comprises heavy chain complementarity determining regions HCDR1, HCDR2, and HCDR3 consisting of the amino acid sequences GYSFTDYNMV (SEQ ID NO: 11), YIDPYNGGTGYNQKFEG (SEQ ID NO: 12), and ARTRDRYDVWYFDV (SEQ ID NO: 13), respectively.

2. An antibody, comprising a light chain (LC) and a heavy chain (HC), wherein the light chain comprises a light chain variable region (LCVR) and the heavy chain comprises a heavy chain variable region (HCVR), wherein the LCVR has the amino acid sequence given in SEQ ID NO: 3, and the HCVR has the amino acid sequence given in SEQ ID NO: 1.

3. The antibody of claim 2, wherein the LC has the amino acid sequence given in SEQ ID NO: 4, and the HC has the amino acid sequence given in SEQ ID NO: 2.

4. The antibody of claim 3, comprising two light chains and two heavy chains, wherein each light chain has the amino acid sequence given in SEQ ID NO: 4, and each heavy chain has the amino acid sequence given in SEQ ID NO: 2.

5. The antibody of claim 4, wherein one of the heavy chains forms an inter-chain disulfide bond with one of the light chains, and the other heavy chain forms an inter-chain disulfide bond with the other light chain, and one of the heavy chains forms two inter-chain disulfide bonds with the other heavy chain.

6. The antibody of claim 5, wherein the antibody is glycosylated.

7. A mammalian cell comprising a DNA molecule comprising a polynucleotide sequence encoding a polypeptide having an amino acid sequence of SEQ ID NO: 4 and a polynucleotide sequence encoding a polypeptide having an amino acid sequence of SEQ ID NO: 2, wherein the cell is capable of expressing an antibody comprising a light chain having an amino acid sequence of SEQ ID NO: 4 and a heavy chain having an amino acid sequence of SEQ ID NO: 2.

8. A process for producing an antibody comprising a light chain having an amino acid sequence of SEQ ID NO: 4 and a heavy chain having an amino acid sequence of SEQ ID NO: 2, comprising cultivating the mammalian cell of claim 7 under conditions such that the antibody is expressed, and recovering the expressed antibody.

9. An antibody produced by the process of claim 8.

10. A pharmaceutical composition, comprising the antibody of any one of claim 1 or 2, and an acceptable carrier, diluent, or excipient.

11. A method of treating cancer, comprising administering to a patient in need thereof, an effective amount of the antibody of any one of claim 1 or 2.

12. The method of claim 11, wherein the cancer is breast cancer, ovarian cancer, gastric cancer, colorectal cancer, or hepatocellular carcinoma.

13. The method of claim 11, further comprising administering simultaneously, separately, or sequentially an effective amount of ramucirumab.

\* \* \* \* \*